United States Patent [19]

Takeya et al.

[11] Patent Number: 4,970,901
[45] Date of Patent: Nov. 20, 1990

[54] METHOD FOR EXAMINING QUALITY OF ADHESION IN VULCANIZED RUBBER-ADHESIVELY BONDED METAL PART

[75] Inventors: Susumu Takeya; Tohru Chikata, both of Tokyo, Japan

[73] Assignee: Arai Seisakusho Co., Ltd., Tokyo, Japan

[21] Appl. No.: 388,576

[22] Filed: Aug. 1, 1989

[30] Foreign Application Priority Data

Nov. 25, 1988 [JP]  Japan .................................. 63-297833

[51] Int. Cl.⁵ .............................................. G01N 3/08
[52] U.S. Cl. .................................................... 73/827
[58] Field of Search .......... 73/150 A, 150 R, 826–830, 73/834, 835, 865.8, 865.9, 827

[56] References Cited

U.S. PATENT DOCUMENTS 4,763,466  8/1988  Abe et al. ............................. 57/213

OTHER PUBLICATIONS

"Tentative Methods of Test for Adhesion of Vulcanized Rubber to Metal", ASTM Designation: D 429-47T, 1947.

Primary Examiner—Robert Raevis

[57] ABSTRACT

In a method for examining the quality of adhesion in a vulcanized rubber-adhesively bonded metal part made by adhesively bonding a rubber member to a metal with an adhesive for rubber applied thereon in a vulcanization-forming or molding, a small rubber test piece is previously vulcanization-formed or molded together with the rubber member onto a portion of the metal surface other than the bonded joint of the rubber member, and the small rubber test piece is teared off from the metal surface, thereby discriminating the part whether the adhesion is good or bad.

5 Claims, 1 Drawing Sheet

METHOD FOR EXAMINING QUALITY OF ADHESION IN VULCANIZED RUBBER-ADHESIVELY BONDED METAL PART

FIELD OF THE INVENTION

The present invention relates to a method for examining the quality of adhesion in a vulcanized rubber-adhesively bonded metal part, such as a gear complete for use in a drive mechanism for a power window in an automobile.

BACKGROUND OF THE INVENTION

In an electric opening and closing drive mechanism for a power window in an automobile, in general, the rotation from a motor is smoothly transmitted to an arm with any shock absorbed, and a gear complete is used for buffering vertical looseness. In manufacturing this type of part, an annular rubber member is stoved, by a vulcanization-forming or molding, between upper and lower disks with an adhesive applied to said disks, thereby providing an integrally-formed part.

In such a vulcanization-forming, a rubber and a metal may be reliably adhesively bonded by a rubber-vulcanizing reaction coinciding in timing with a reaction of a metal plate and the adhesive. Therefore, a failure of adhesion may be produced in some cases with an inferior timing between the rubber-vulcanizing reaction and the reaction of the metal plate and the adhesive in a process of mass production of such parts.

The failure of adhesion may be also produced due to inadequate application of adhesive, an excessive thermal treatment in an adhesive drying step, adhesion of a release agent on a bonded surface, adhesion of a material disturbing the adhesion properties such as fats and oils, and the like.

Thereupon, the following methods have conventionally been adopted: a method for estimating the failure of adhesion for a population of formed products by picking up a small number of parts from the population and subjecting them to an adhesion rupture test in which a thrust force is applied between the rubber member and the metal disk; and a method for examining the failure of adhesion by applying, to all of products, a stress as low as not to exert any practical influence without providing any damage.

In the above rupture test involving the picking-up, however, the adhesion properties of all the products are not necessarily assured. On the other hand, in the method for estimation by applying the low stress, the products whose parts have been slightly adhesively bonded can be estimated, but if the parts have been adhesively bonded by a stronger adhesive force than the low stress applied for estimating, then it is impossible to detect a possibility of a failure of adhesion for products in which components are bonded somewhat but with an incomplete adhesion and hence, adhesion-defective products have often flowed into the market.

BRIEF SUMMARY OF THE INVENTION

The present invention has been accomplished with such circumstances in view, and it is an object of the present invention to provide a method for examining the quality of adhesion in a vulcanized rubber-adhesively bonded metal part, wherein all the products can be extremely simply and exactly discriminated whether the adhesion is good or bad, without damaging the rubber member, thereby ensuring that marketing of adhesion-defective products can be reliably prevented.

According to the present invention, the above object is achieved by providing a method for examining the quality of adhesion in a vulcanized rubber-adhesively bonded metal part made by adhesively bonding a rubber member to a metal part with an adhesive for rubber applied thereon in a vulcanization-forming or molding, comprising previously vulcanization-forming or molding a small rubber test piece together with the rubber member onto a portion of the metal surface other than the bonded joint of the rubber member, and tearing off the small rubber test piece from the metal surface, thereby discriminating the part whether the adhesion is good or bad.

With the method having the above feature according to the present invention, the adhesion is discriminated whether good or bad by tearing off the small rubber test piece from the metal surface and therefore, it is possible to extremely simply and exactly examine all the products whether the components are bonded or not; for the magnitude of adhesive force; whether the adhesion is good or bad; or for the cause of a failure of adhesion. This makes it possible to previously prevent flowing or marketing of adhesion-defective products, as well as the subsequent generation of defective products by knowing the cause of the adhesion failure.

DETAILED DESCRIPTION OF THE EMBODIMENTS

The present invention will now be described by way of an embodiment in which the present invention is applied to a gear complete shown in the Figures. A gear complete 1, which is to be examined or discriminated whether the adhesion is good or bad, is integrally formed by a vulcanization forming in which an annular rubber member 3 is stoved between an upper and a lower metal disk 2 and 2' with an adhesive applied on their entire surface.

A small test piece 4 such as a small projection, which has been vulcanization-formed or molded concurrently with the vulcanization forming or molding of the rubber member 3 by introducing a rubber material, is mounted on a portion of a surface of the metal disk 2 or 2', which is not a surface having the rubber member 3 bonded thereon.

Figure 1:
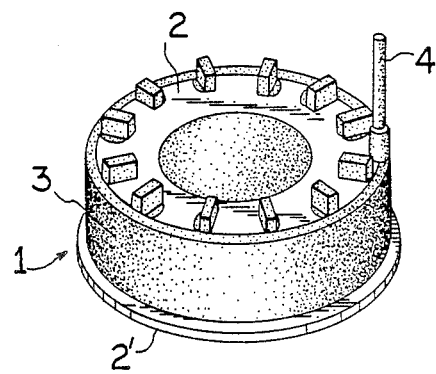
FIG. 1 is a perspective view of one example of a part to be examined according to the present invention.
Figure 2:
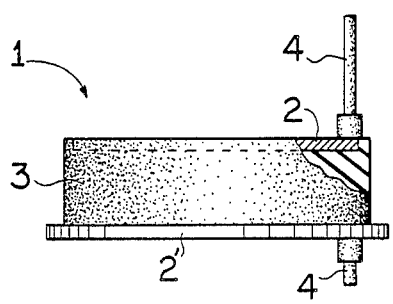
FIG. 2 is a front view of the part to be examined, shown in FIG. 1.
Figure 3:
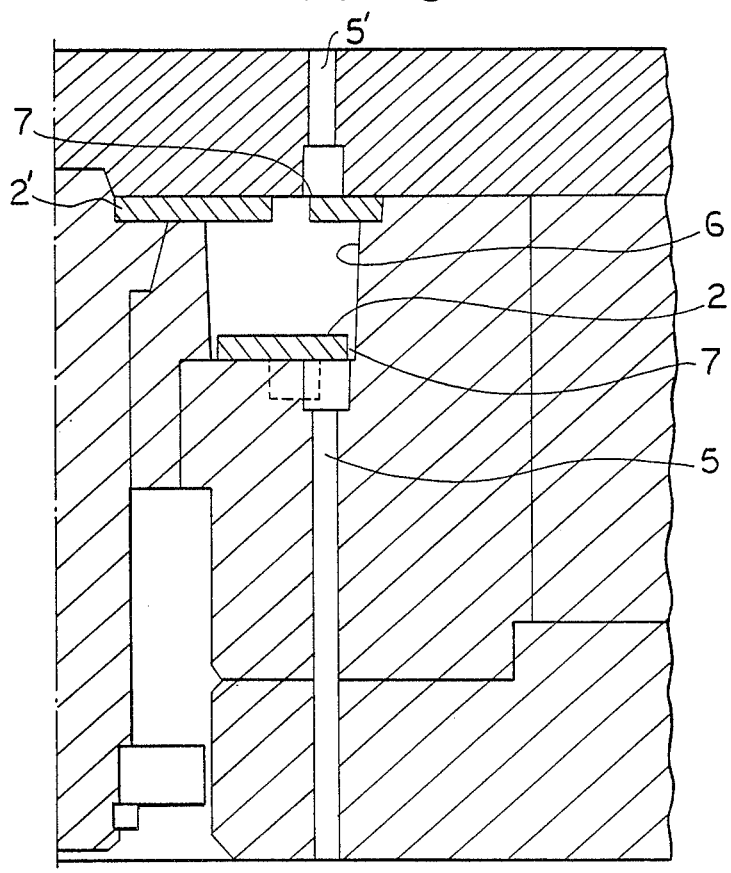
FIG. 3 is a partially longitudinal sectional view of the part shown in FIG. 1 as being formed.

FIG. 3 illustrates one example of a mold for forming the gear complete 1. The mold is constructed in the following manner: Small test piece forming spaces 5 and 5' are created so that their opened base ends come into contact with the surfaces of the metal disks 2 and 2' placed into the mold. Inlet openings 7 for introducing a portion of a rubber material poured into and filled in a cavity 6 for forming the rubber member 3 are provided at a portion of each of the opened base ends of the small test piece forming spaces 5 and 5'. Thus, when the rubber material poured and filled in the cavity 6 for forming the rubber member 3 is introduced into the small test piece forming spaces 5 and 5', the rubber material filled therein comes into contact with the metal disks 2 and 2' at the opened base ends of the small test piece forming spaces 5 and 5' and is then stoved between the metal disks 2 and 2' with the adhesive interposed therebetween concurrently with the vulcanization forming of the rubber member 3.

Therefore, the rubber material 3 and the small test piece 4 are concurrently vulcanization-molded under the same conditions with the same adhesive and hence, if the small test piece 4 is discriminated whether the adhesion is good or bad, it results in that the rubber member 3 have been also discriminated whether the adhesion is good or bad.

In such examination of the quality of adhesion in the small test piece 4, it is possible to exactly examine the part whether the adhesion is good or bad of the adhesion, not only for presence or absence of the adhesion but also for the magnitude of adhesive force, or even for the cause of an adhesion failure, by estimating adhesively bonded conditions of the small test piece in various examinations, such as by judging the presence or absence or amount of retention of the rubber remaining on the metal disks 2 and 2' when the small test piece 4 has been teared off from the metal disks 2 and 2' at the base end after forming of each gear complete 1.

The objects to be examined according to the present invention are not limited to the gear complete, and it will be understood that the present invention is applicable to a wide variety of parts made by adhesively bonding a rubber member to a metal with an adhesive interposed therebetween in a vulcanization forming process, as in the aforesaid gear complete.

What is claimed is:

1. A method for examining the quality of adhesion for vulcanized rubber adhesively bonded to a metal part in a product made by adhesively bonding a rubber member to a metal surface, with an adhesive for rubber applied to said surface, in a vulcanization-forming or molding, said method for examining comprising vulcanization-forming or molding a small rubber test piece together with said rubber member onto a portion of the metal surface of said product other than a portion of said surface to be bonded to said rubber member, and tearing off the small rubber test piece from the metal surface to determine whether the adhesion is good or bad.

2. In a method of manufacturing comprising the steps of:
    (a) pouring unvulcanized rubber into a mold to form a rubber member and simultaneously contacting said member with a metal part having a metal surface with adhesive applied to said surface, and
    (b) vulcanizing said rubber member and simultaneously adhering said member to said metal surface, the improvement comprising:
    (i) at step (a), pouring additional unvulcanized rubber into said mold to form a rubber test piece contacting said metal surface at an area of said surface not to be contacted by said rubber member,
    (ii) at step (b), vulcanizing and adhering said small test piece to said metal surface at the same time as said vulcanization and adherence of said rubber member, and
    (iii) tearing off said vulcanized rubber test piece from the metal surface to determine the quality of adhesion of said vulcanized rubber member to said metal surface.

3. The improved method of claim 2 wherein said determination of quality of adhesion comprises determining a magnitude of adhesive force.

4. The improved method of claim 2 wherein said determination of quality of adhesion comprises determining what amount of rubber from said test piece remains adhered to the metal surface after said tearing off.

5. The method of claim 2 wherein said determining of the quality of adhesion comprises determining cause of adhesion failure.

* * * * *